United States Patent
Tokita (10) Patent No.: US 9,239,316 B2
(45) Date of Patent: Jan. 19, 2016

(54) OBJECT INFORMATION ACQUIRING APPARATUS

(75) Inventor: Toshinobu Tokita, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 365 days.

(21) Appl. No.: 13/820,564

(22) PCT Filed: Sep. 6, 2011

(86) PCT No.: PCT/JP2011/070679
§ 371 (c)(1),
(2), (4) Date: Mar. 4, 2013

(87) PCT Pub. No.: WO2012/036106
PCT Pub. Date: Mar. 22, 2012

(65) Prior Publication Data
US 2013/0167648 A1    Jul. 4, 2013

(30) Foreign Application Priority Data

Sep. 13, 2010  (JP) ................................. 2010-204380
Aug. 5, 2011   (JP) ................................. 2011-171913

(51) Int. Cl.
*G01N 29/24* (2006.01)
*A61B 5/00* (2006.01)
(Continued)

(52) U.S. Cl.
CPC .............. *G01N 29/24* (2013.01); *A61B 5/0095* (2013.01); *A61B 8/0825* (2013.01); *A61B 8/40* (2013.01);
(Continued)

(58) Field of Classification Search
CPC ........ A61B 5/0095; A61B 8/40; A61B 8/429; A61B 8/5269; A61B 8/0825; A61B 8/4209; A61B 8/485; G01N 29/07; G01N 29/24; G01N 2291/0245; G01S 15/8945

USPC ........................................................... 73/655
See application file for complete search history.

(56) References Cited

U.S. PATENT DOCUMENTS 4,210,028 A * 7/1980 Hildebrand ..................... 73/598
5,557,048 A * 9/1996 Koike et al. .................... 73/597
(Continued)

FOREIGN PATENT DOCUMENTS

CN    1798524    7/2006
CN    1890531    1/2007
(Continued)

OTHER PUBLICATIONS

S. Manohar et al., "The Twente Photoacoustic Mammoscope: System Overview and Performance", *Physics in Medicine and Biology*, 50, pp. 2543-2557 (2005).
(Continued)

*Primary Examiner* — J M Saint Surin
(74) *Attorney, Agent, or Firm* — Fitzpatrick, Cella, Harper & Scinto (57) ABSTRACT

An object information acquiring apparatus has: a holding unit which holds an object; a probe which receives an acoustic wave generated in the object via the holding unit and converts the acoustic wave to an electrical signal; a force measuring unit which measures a force applied to the object when the object is held by the holding unit; a sound speed acquiring unit which determines a sound speed in the object by using the force measured by the measuring unit and a contact area between the object and the holding unit; and a generating unit which generates object information data from the information about the sound speed determined by the sound speed acquiring unit and the electrical signal.

21 Claims, 8 Drawing Sheets

(51) Int. Cl.
*A61B 8/08* (2006.01)
*A61B 8/00* (2006.01)
*G01N 29/07* (2006.01)
*G01S 15/89* (2006.01)

(52) U.S. Cl.
CPC ............... *A61B 8/4209* (2013.01); *A61B 8/429* (2013.01); *G01N 29/07* (2013.01); *G01S 15/8945* (2013.01); *A61B 8/485* (2013.01); *A61B 8/5269* (2013.01); *G01N 2291/02475* (2013.01); *G01N 2291/02827* (2013.01)

(56) References Cited

U.S. PATENT DOCUMENTS

| | | | |
|---|---|---|---|
| 5,603,326 A | 2/1997 | Richter | 600/443 |
| 5,678,565 A | 10/1997 | Sarvazyan | 600/583 |
| 8,540,637 B2 | 9/2013 | Tokita et al. | 600/443 |
| 2006/0025682 A1 | 2/2006 | Vanderby et al. | 600/438 |
| 2006/0136152 A1* | 6/2006 | Takahashi | 702/42 |
| 2007/0032726 A1 | 2/2007 | Osaka et al. | 600/459 |
| 2007/0098251 A1 | 5/2007 | Lu | 382/154 |
| 2009/0234229 A1* | 9/2009 | Mikami et al. | 600/445 |
| 2010/0030078 A1* | 2/2010 | Mikami | 600/443 |
| 2010/0081935 A1 | 4/2010 | Matsumura et al. | 600/443 |
| 2011/0230762 A1 | 9/2011 | Tokita et al. | 600/437 |
| 2011/0245667 A1 | 10/2011 | Tokita | 600/437 |
| 2012/0150012 A1 | 6/2012 | Fujimoto et al. | 600/437 |
| 2012/0238859 A1 | 9/2012 | Tokita et al. | 600/437 |
| 2012/0302865 A1 | 11/2012 | Tokita et al. | 600/437 |
| 2013/0061678 A1 | 3/2013 | Yamamoto et al. | 73/602 |

FOREIGN PATENT DOCUMENTS

| | | | |
|---|---|---|---|
| CN | 101008606 | | 8/2007 |
| CN | 101511275 | | 8/2009 |
| CN | 101666782 | | 3/2010 |
| EP | 0719520 A2 | | 7/1996 |
| JP | 2786334 | | 5/1998 |
| JP | 2786334 | | 8/1998 |
| JP | 2010-267158 | | 8/2010 |
| JP | 2012100997 | * | 5/2012 |
| WO | WO 94/05993 A2 | | 3/1994 |
| WO | WO 2010/074103 A1 | | 7/2010 |

OTHER PUBLICATIONS

Office Action issued on Apr. 30, 2014, in Chinese (P.R. China) counterpart application 201180043240.4, with translation.
Office Action issued on Feb. 28, 2015, in Chinese (P.R. China) counterpart application 201180043240.4, with translation.

* cited by examiner

OBJECT INFORMATION ACQUIRING APPARATUS

TECHNICAL FIELD

The present invention relates to an object information acquiring apparatus which creates an image of an acoustic wave generated in an object.

BACKGROUND ART

An object information acquiring apparatus (photoacoustic apparatus) which was developed for use in investigating breast cancer has been described in Non Patent Literature 1. In Non Patent Literature 1, an object (breast) is compressed between a glass plate and an ultrasound probe, and illumination light (near-infrared light) using an Nd: YAG laser as a light source is irradiated onto the breast through the glass plate. The photoacoustic wave generated inside the object (breast) is received by the ultrasound probe, and the internal tissue of the object (breast), and in particular, the generation of new blood vessels in breast cancer, is reconstructed as an image and displayed. When image reconstruction is carried out in this way, the speed of sound in the object is used in calculation. In general, the average speed of sound in a breast is considered to be 1510 m/s. Using photoacoustic wave in this way to reconstruct an image is called PAT (Photoacoustic tomography).

However, in the apparatus in Non Patent Literature 1, there is no mention of correcting change in the speed of sound of the object (breast). Therefore, if the supposed speed of sound is different from the speed of sound in the object, then this gives rise to decline in resolution. Therefore, desirably, change in the speed of sound is corrected. Patent Literature 1 is one method of this kind.

Figure 5:
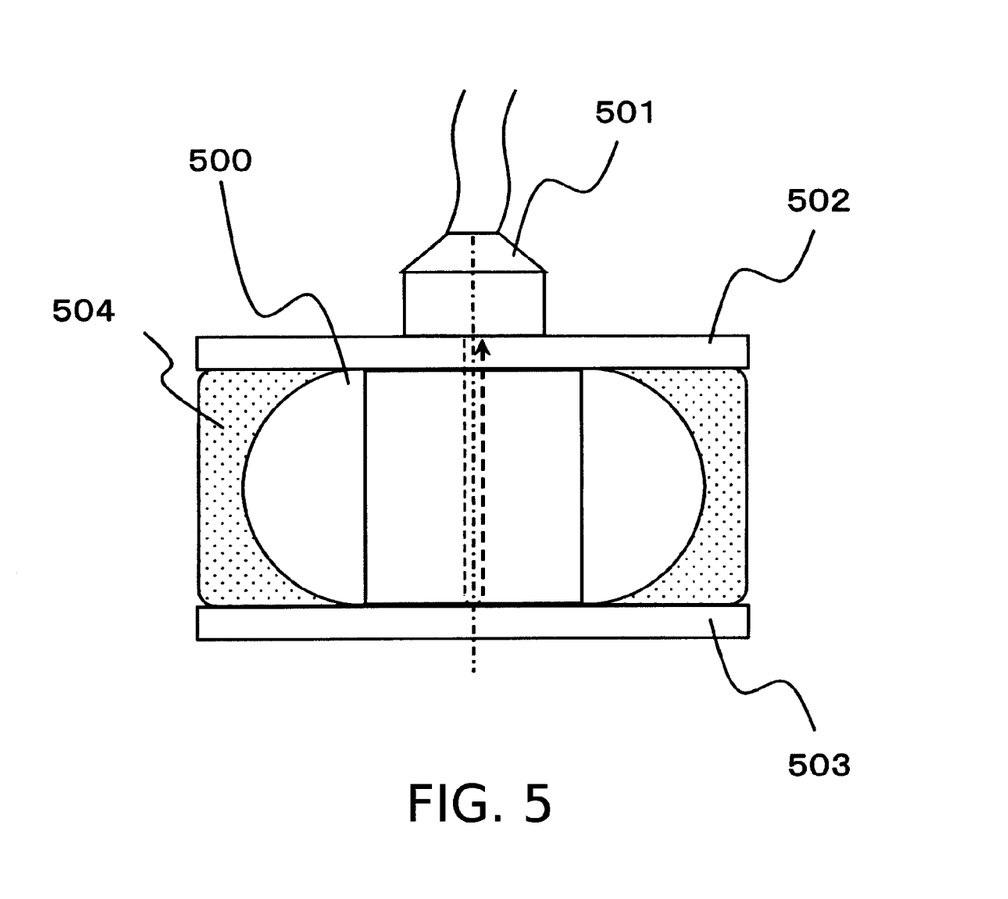
FIG. 5 is a diagram describing background art technology.

FIG. 5 shows an approximate view of Patent Literature 1, in which a holding plate 502 which transmits a ultrasound wave and a compression plate 503 which reflects the ultrasound wave are provided, and a probe 501 transmits an ultrasound beam onto an inspection object 500. An echo signal which is transmitted through the holding plate 502 and is reflected by the compression plate 503 is received by the probe 501 and recorded. A unit is provided which extracts the propagation time and/or amplitude from this echo signal, and evaluates same by comparison with a propagation time and/or amplitude of a reference echo signal. In this case, it is possible to calculate an average speed of sound on the basis of the propagation time and the interval between the compression plate 503 and the holding plate 502.

CITATION LIST

Patent Literature

PTL1: Japanese Patent No. 2786334

Non Patent Literature

NPL1: Srirang Manohar, et al., The Twente photoacoustic mammoscope: system overview and performance, Physics in Medicine and Biology 50 (2005) 2543-2557.

SUMMARY OF INVENTION

Technical Problem

However, there are problems of the following kind in conventional technology.

According to Patent Literature 1, it is possible to determine the speed of sound. However, in the calculation process, it is necessary to account for the propagation time of the ultrasound echo propagating through a bonding medium 504 and a matching layer of the probe 501, for example, apart from the holding plate 502. Patent Literature 1 does not discuss this issue, and therefore it is not possible to calculate the speed of sound accurately. Furthermore, if the distance between the compression plate 503 and the holding plate 502 is increased, the signal is attenuated inside the object 500, and therefore the signal reflected by the compression plate 503 becomes small and measurement is difficult. In other words, if the object 500 is large, then the speed of sound cannot be measured. Moreover, the method of determining the speed of sound based on Patent Literature 1 can only be applied to a parallel flat plate compression holding method (a method which compresses the object 500 by means of a compression plate 503 and a holding plate 502).

The present invention was devised in view of the problem described above, an object thereof being to provide technology for suitably determining the speed of sound in an inspection object, in an object information acquiring apparatus.

Solution to Problem

In order to solve the problem described above, the present invention provides an object information acquiring apparatus, comprising:
a holding unit which holds an object;
a probe which receives an acoustic wave generated in the object via the holding unit and converts the acoustic wave to an electrical signal;
a force measuring unit which measures a force applied to the object when the object is held by the holding unit;
a sound speed acquiring unit which determines a sound speed in the object by using the force measured by the measuring unit and a contact area between the object and the holding unit; and
a generating unit which generates object information data from the information about the sound speed determined by the sound speed acquiring unit and the electrical signal.

The present invention also provides an object information acquiring apparatus, comprising:
a holding unit which holds an object;
a probe which receives an acoustic wave generated in the object via the holding unit and converts the acoustic wave to an electrical signal;
a force measuring unit which measures a force applied to the object when the object is held by the holding unit;
an area measuring unit which determines a contact area between the object and the holding unit by use of light or acoustic wave;
a processing unit which calculates a stress on the object by use of the force measured by the force measuring unit and the contact area between the object and the holding unit.

Advantageous Effects of Invention

According to the present invention, it is possible to provide technology for accurately determining the speed of sound in an object, in an object information acquiring apparatus.

Further features of the present invention will become apparent from the following description of exemplary embodiments with reference to the attached drawings.

DESCRIPTION OF EMBODIMENTS

The object information acquiring apparatus measures at least an acoustic wave (typically, an ultrasound wave) generated from at least an object (breast), by means of an ultrasound wave probe, through the object holding plate. The object is held by a holding plate, the force applied to the object and the contact area between the holding plate and the object are measured, and the average speed of sound inside the object is determined from these measurement values, by referring to a calculation formula or table. Object information data is generated from the ultrasound wave signal received by the probe and the determined speed of sound information. In the examples given below, the object is a living organism, such as a breast, and a living organism information acquiring apparatus is described, but the object under measurement is not limited to a living organism information acquiring apparatus. The present invention can be applied to an object information acquiring apparatus for use with various measurement objects. Moreover, in the present invention, the speed of sound in the object means the speed of propagation of an acoustic wave which propagates inside the object.

The object information indicates information reflecting variation in the acoustic impedance of the internal tissue of the object, the distribution of acoustic wave generating sources, the distribution of the initial sound pressure inside the object, or the distribution of the light energy absorption density which is derived from the distribution of the initial sound pressure, the absorption coefficient distribution, and the density distribution of the material which constitutes the tissue. The distribution of material density is, for example, the distribution of oxygen saturation, the distribution of oxidized/reduced hemoglobin density, and the like. The object information data is data based on these object information elements: for example, it may be numerical data of various types, or data for generating an image of the object by visualizing the numerical data of various types described above.

Next, photoacoustic mammography (hereinafter, called PAM) is described as one example of a living organism information acquiring apparatus (object information acquiring apparatus).

Figure 4:
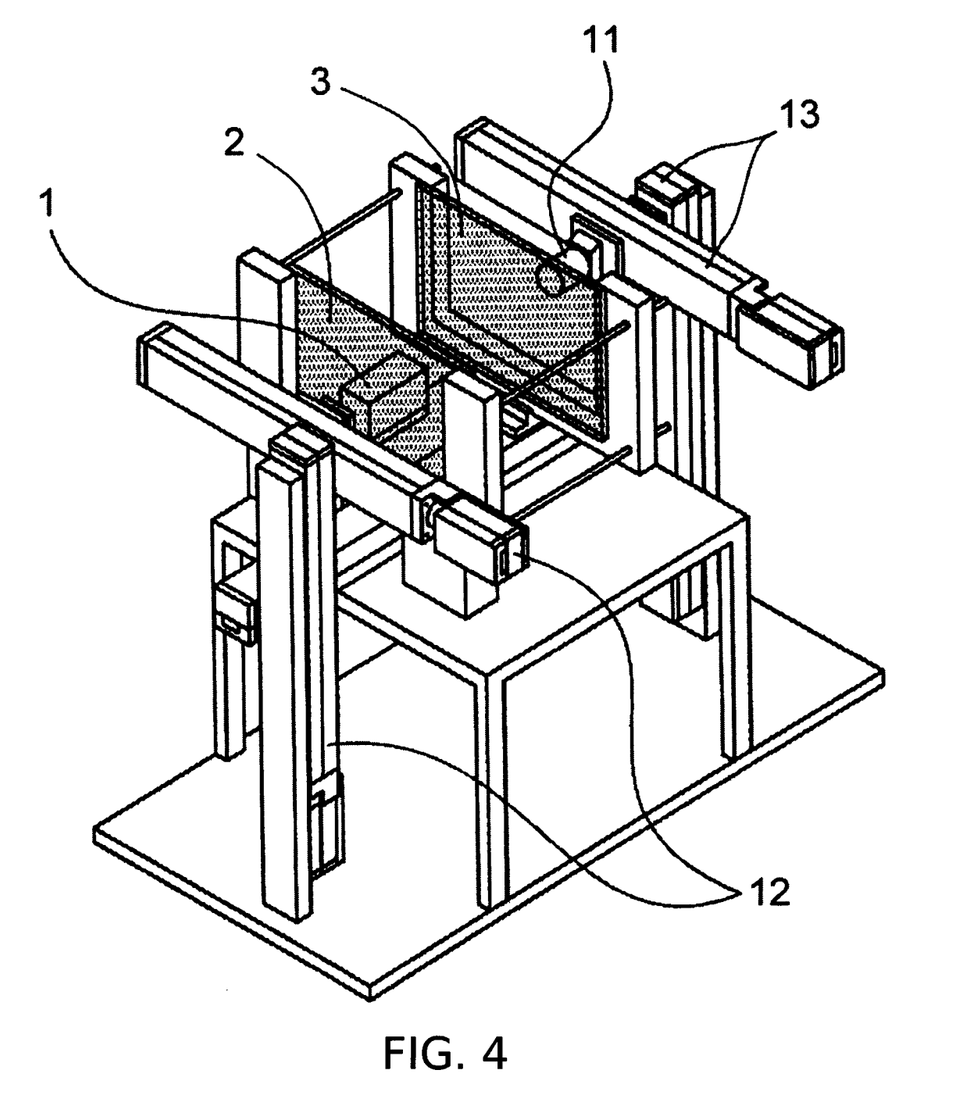
FIG. 4 is a diagram describing an object information acquiring apparatus.

FIG. 4 is a diagram of PAM where the principles of photoacoustic tomography (PAT) are applied to a breast inspection apparatus. Since a photoacoustic wave can acquire images of blood and blood vessels, specifically, then images of blood vessels produced by new generation of cancerous blood vessels can be captured. FIG. 4 shows the main part of a composition where this principle is applied to the diagnosis of breast cancer.

In FIG. 4, the probe 1 serves to receive a photoacoustic wave generated from the object (not illustrated). The holding plate 2 serves to hold the object, and the probe 1 receives the photoacoustic wave generated from the object, via the holding plate 2. The material of the holding plate is desirably PMP (polymethylpentene), but it is also possible to substitute other resins. A compression plate 3 compresses and holds the object by adjusting the gap with respect to the holding plate 2. The material of the compression plate 3 is desirably a resin such as acrylic or polycarbonate, or a glass such as quartz. An illumination optical system 11 irradiates pulse light having a wavelength of approximately 650 nm to 1100 nm, and causes a photoacoustic wave to be generated from the object. The light source and the path of the illumination light from the light source to the illumination optical system 11 are not illustrated. A probe scan unit 12 performs a scanning action of a probe 1 in the planar direction of the holding plate, and the illumination light scanning unit 13 performs a scanning action of the illumination light optical system 11 in the planar direction of the compression plate.

The present invention is described by taking PAM as an example, but the invention is not limited to this, and the present invention can also be applied to an ultrasound echo apparatus or a transmissive type ultrasound apparatus, provided that the apparatus is one which receives an ultrasound wave from an object by a probe 1 through the holding plate 2. In the ultrasound echo apparatus, a focused ultrasound wave beam may be transmitted and received by the probe 1, and in the case of a transmissive type ultrasound apparatus, a transmitting probe may be provided instead of the illumination optical system 11.

Below, in Example 1, a method is described for determining the speed of sound in a mode where an object is compressed and held by using two parallel plates which form a holding unit. In Example 2, a method is described for determining the speed of sound in a mode where an object is pressed on a holding plate. In Example 3, a method is described for correcting refraction which occurs at the interface between a holding plate and an object, using the determined speed of sound.

Example 1

Figure 1A:
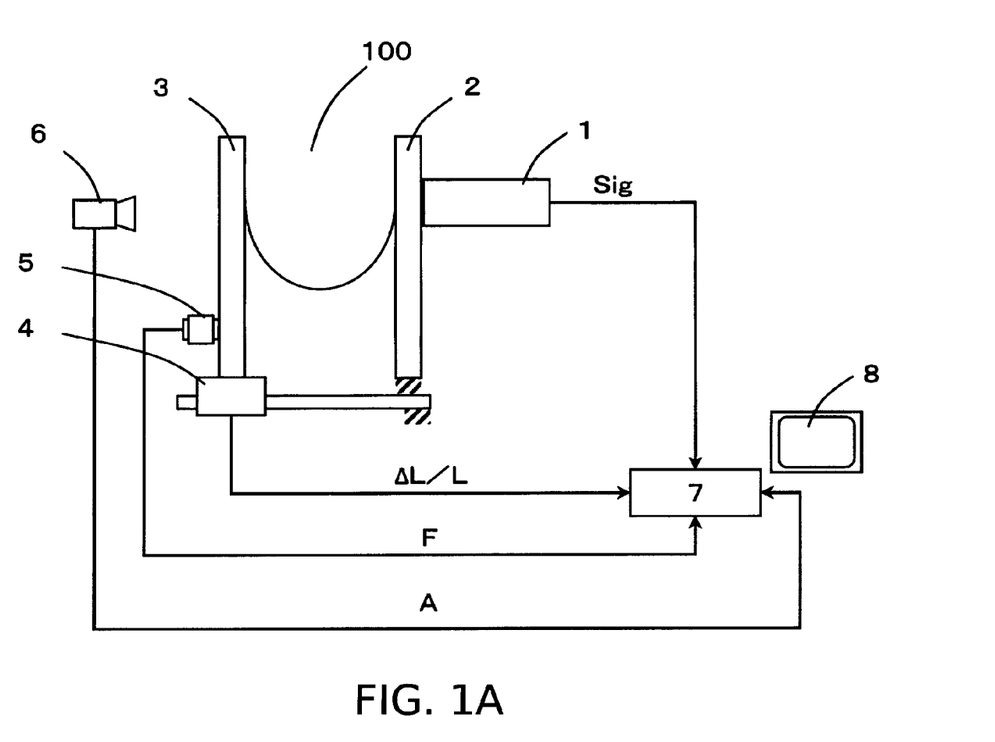
FIG. 1A is a diagram describing the apparatus composition of Example 1.

FIG. 1A is a diagram showing an apparatus composition based on a parallel flat plate system. In this system, an object (breast) 100 is inserted and sandwiched between a holding plate 2 and a compression plate 3 and is measured by using an ultrasound wave. The probe 1 is able to receive at least an ultrasound wave generated from the object 100. The holding plate 2 serves to hold the object 100. The probe 1 has a plurality of elements which respectively receive an ultrasound wave generated from the object 100, through the holding plate 2, and convert the ultrasound wave into an electrical signal (reception signal). The received signal Sig which has been converted is sent to the processing unit 7, which is described below. The probe 1 is also mounted on a probe scanning unit, which is not illustrated. The compression plate 3 sandwiches the object 100 against the holding plate 2, and the object 100 is compressed or released from compression by operation of the compression plate 3.

The linear scale 4 is a distance measuring unit which measures a distance L between the holding plate 2 and the compression plate 3. In the present example, a linear scale 4 was used as the distance measuring unit, but it is also possible to employ another sensor. The load cell 5 is a force measuring unit which measures a force applied to an object (the compression force F in Example 1), when the object 100 is held and compressed. In the present example, a load cell 5 which measures the reactive force from the object when the object is compressed is used as a force measuring unit, but the invention is not limited to this and it is also possible to employ another sensor. Furthermore, as the force applied to the object, the pressure measuring unit may also measure the force actually applied to the object via the compression plate, rather than just the reactive force from the object when the object is compressed.

Figure 1B:
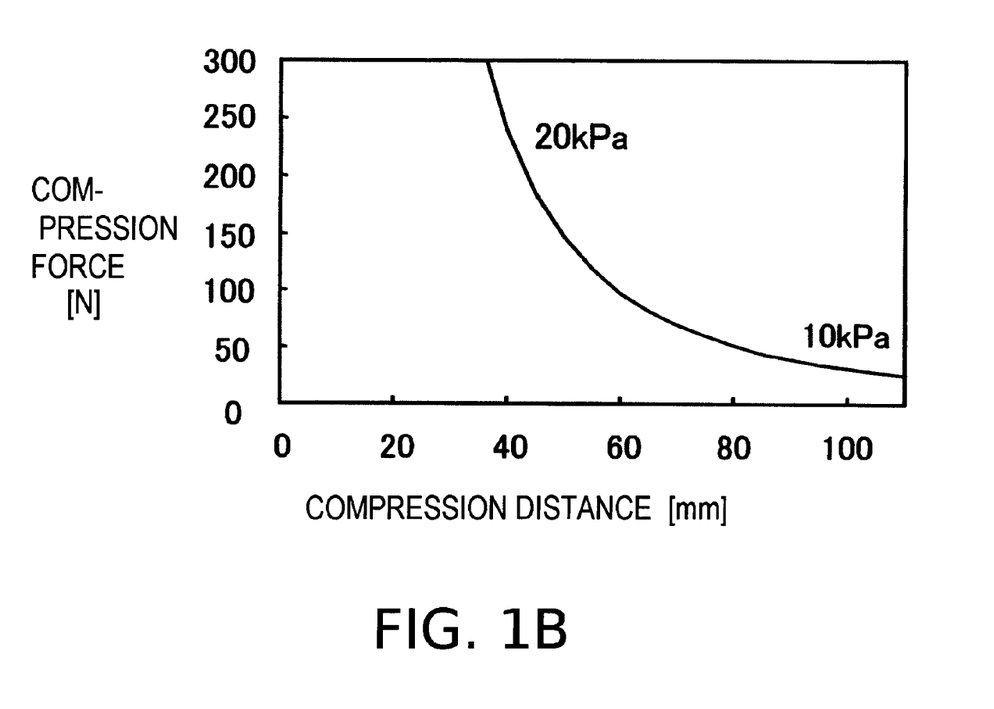
FIG. 1B is a diagram describing the effects of compression and holding in Example 1.
Figure 1C:
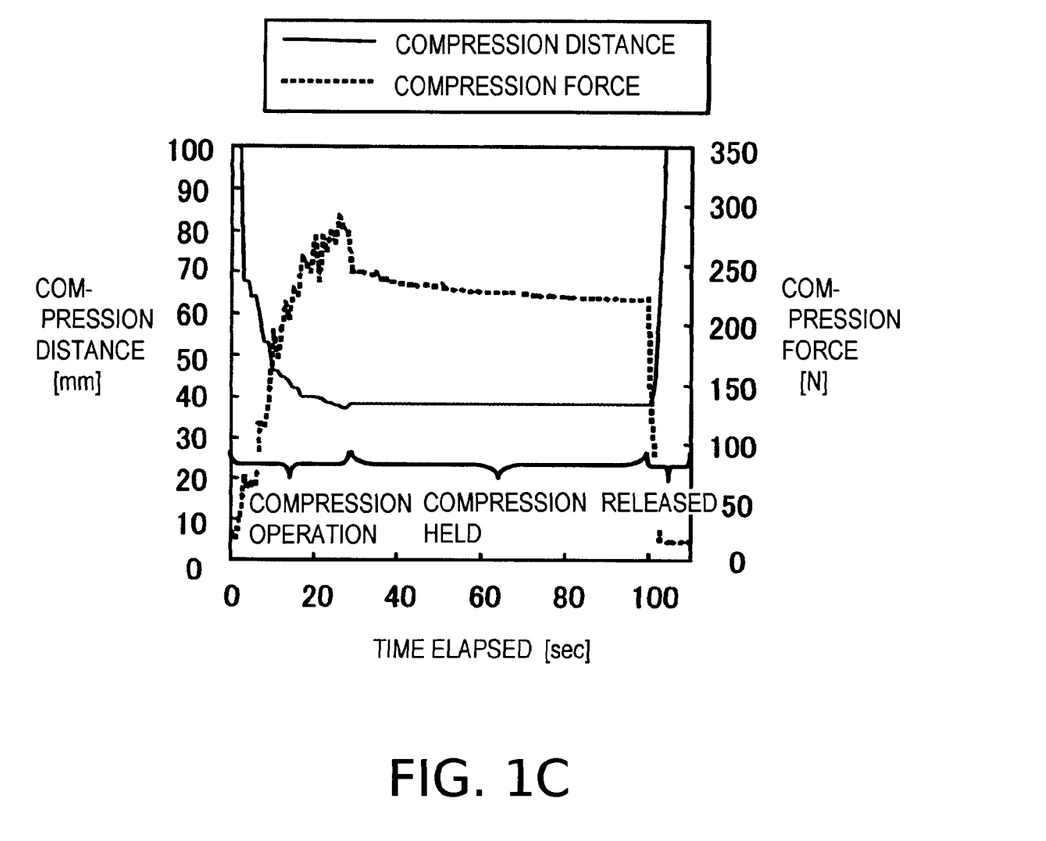
FIG. 1C is a further diagram describing the effects of compression and holding in Example 1.

FIG. 1C shows a graph in which elapsed time is plotted on the horizontal axis, and the compression distance and the compression force are plotted on the vertical axis, for a case where the object 100 is gradually compressed and held by the apparatus in FIG. 1A. FIG. 1B shows the compression distance and the compression force during a compression operation, plotted respectively on the horizontal axis and the vertical axis. The gradient of the line in FIG. 1B indicates the elastic modulus (Young's modulus) and the numerical values on the graph are elastic modulus values. The following Formulas (1) to (3) were used in calculation.

Hooke's law σ=Eε (σ: stress; ε: strain; E: Young's modulus)   (1)

σ=F/A (F: compression force; A: compression surface area)   (2)

ε=ΔL/L (L: length before compression (F=0); ΔL: amount of displacement before and after compression)   (3)

From FIG. 1B, it can be seen that, with the compression and holding action, in other words, as the compression distance becomes smaller, the change in the compression force becomes larger in relation to the change in the compression distance. In other words, the elastic modulus progressively increases. More specifically, provided that the stress σ and the strain ε can be determined, then it is also possible to calculate Young's modulus E. The strain ε is determined by measuring the distance between the plates before and after deformation by a linear scale 4. Furthermore, the stress σ can be calculated from the compression force F determined by the load cell 5 and the compression surface area A. The compression surface area A is the contact area between the object and the holding plate (or between the object and the compression plate), and is measured by a surface area measuring unit. As shown in FIG. 1A, desirably, a camera 6 is installed and the compression surface area A is calculated from the captured image data. In this case, the camera which captures images and the processing unit which performs calculation function as a surface area measuring unit for determining the compression surface area A and calculate the compression surface area by use of light.

The measurement of the compression surface area is not limited to a method which calculates the compression surface area A on the basis of a camera 6 and image data. For example, an ultrasound wave is transmitted and received while scanning the probe 1 with a probe scanning unit (which is not illustrated), and if the received signal passes through the object 100 and a signal reflected from the compression plate 3 can be received, then it is judged that an object 100 is present. If there is only a signal reflected from the holding plate 2, then it is judged that there is no object 100. It is also possible to adopt a method which judges the presence or absence of an object 100 from the reflection time and determines the compression surface area A, by comparison with the position information of the probe scanning unit in this way. Apart from this, it is also possible to use an optical sensor, or the like.

As described above, the contact area between the object and the holding unit is obtained by optical measurement or by acoustic measurement in this invention. The reason why such measurement method is adopted in the present invention is that, when acquiring the object information in the present invention, the acoustic waves can not be properly received by arranging pressure sensors on the whole face of the holding unit for measuring the contact area, because acoustic waves are received via the holding unit and then object information is acquired. Therefore, in the present invention, it is preferable to calculate the contact area with a processing unit, by use of light information obtained from a camera or an optical sensor, or by use of received signals obtained by transmitting and receiving ultrasound waves (acoustic waves). Moreover, it is able to calculate the contact area with a processing unit by use of received signals of photoacoustic waves generated from an object irradiated with light Furthermore, as shown in FIG. 1C, during compression and holding, the compression force diminishes over time after the compression and holding action has been completed. Therefore, desirably, the speed of sound is calculated from the compression force during reception of the acoustic wave used in generating object information data.

Next, the method of calculating the speed of sound from the elastic modulus (Young's modulus) will be described. In FIG. 1A, the processing unit 7 receives compression distance information (information about the distance between the two plates) from the linear scale 4, compression force information (F) from the load cell 5, and image data from the camera 6. In this, the compression surface area (A) can be determined on the camera side and sent to the processing unit, and image processing can be carried out in the processing unit to determine the compression surface area. The elastic modulus of the object 100 and the average speed of sound inside the object are calculated. The average speed of sound is calculated using the following Formula (4).

[Math. 1]

$$c = \sqrt{\frac{1-v}{(1+v)(1-2v)}} \sqrt{\frac{E}{\rho}} \quad (4)$$

Here, c is the average speed of sound and E is Young's modulus. ρ is the density, for example, 1020 kg/m³. v is Poisson's ratio, which is a value close to 0.5.

Furthermore, if the elastic modulus is calculated, then the average speed of sound can be calculated as a function c(E) of the elastic modulus, by multiplying the square root of the rate of change from the standard elasticity, by a standard speed of sound. For example, if the object 100 is a breast, then the standard average speed of speed is 1510 m/s and the standard elastic modulus is 10 kPa. Therefore, it is possible to calculate the average speed of sound by subtracting the standard elastic modulus 10 kPa from the calculated elastic modulus and multiplying the square root of this figure by the standard average speed of sound, 1510 m/s.

Moreover, the processing unit 7 may employ a method in which a memory is prepared in advance to store a table containing the compression distance, the compression force and the compression surface area as variables, and the speed of sound is determined from the measurement results by referring to this table. Furthermore, since there is a correlation between the stress and the speed of sound, a memory can be prepared to store a table containing stress as a variable, and the speed of sound can be determined by referring to this table on the basis of the measured compression surface area and the measured compression force.

Next, the processing unit 7 receives an electrical signal (Sig) from the probe 1, and generates object information data on the basis of the electrical signal and the determined average speed of sound information. This data is then shown on the monitor 8.

In the present example, the holding plate and the compression plate correspond to the holding unit of the present invention. An acoustic wave is received by the probe, through the holding unit. The load cell corresponds to a force measuring unit. The linear scale corresponds to a distance measuring unit. The camera corresponds to a surface area measuring unit. The processing unit corresponds to a sound speed acquiring unit which determines the speed of sound, and to a generating unit which generates object information data.

In this way, according to Example 1, it is possible to determine the average speed of sound with high accuracy, even in cases where the object 100 is large, and the distance between the holding plate 2 and the compression plate 3 is large. Therefore, it is possible to improve the resolution of imaging carried out on the basis of the received signal in the processing unit 7.

Moreover, the information of the stress, obtained by use of the contact area between the object and the holding plate and the compression force, can be used for the purpose other than calculation for sound speed in the present invention.

Example 2

In Example 1, a parallel flat plate compression and holding method was described. Example 2 describes measurement based on a holding method which presses an object 100 against a holding plate 2.

Figure 2A:
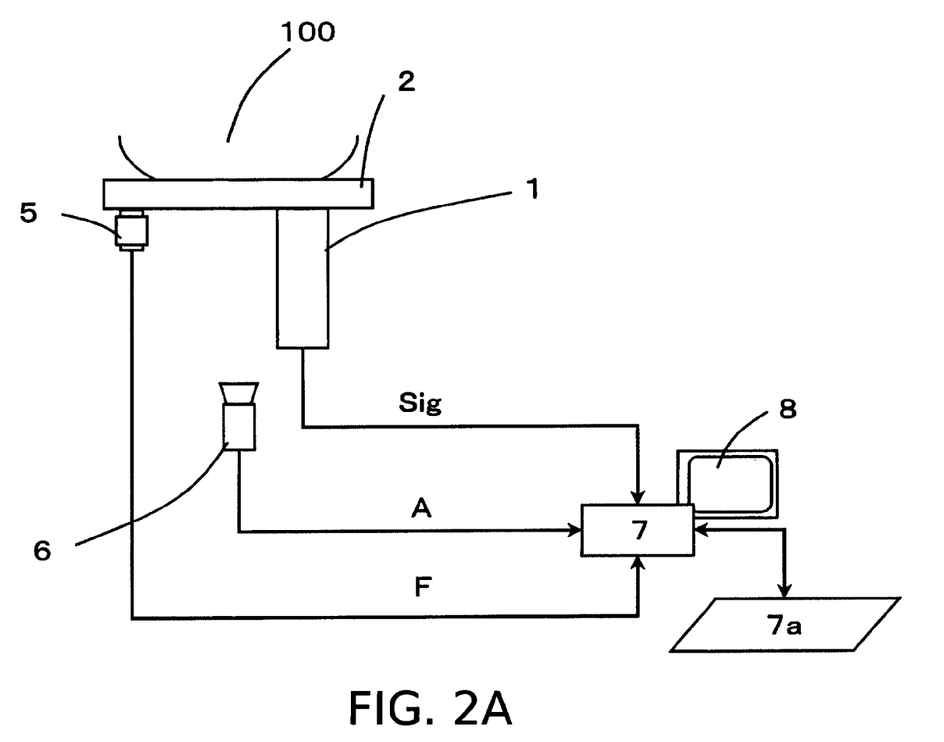
FIG. 2A is a diagram describing the apparatus composition of Example 2.

In FIG. 2A, an object 100 is held by being pressed against the holding plate 2, which is a holding unit. In FIG. 2A, the object 100 is shown as being pressed against the holding plate 2 from above, but the direction is not limited to this. Moreover, the holding plate 2 is depicted as a flat-surfaced member, but is not limited to this and may also be a member having a cup shape, for example.

Next, a probe 1 mounted on a probe scanning unit (not illustrated) receives an ultrasound wave generated from the object 100, through the holding plate 2. The received signal is converted into an electrical signal (Sig) which is then sent to a processing unit 7 (described hereinafter). A load cell 5 forms a force measuring unit, which measures the force (F) applied to the object when the object 100 is pressed against the holding plate 2. A camera 6 functions as a surface area measurement unit for determining the contact area (A) between the object and the holding plate when the object 100 is pressed.

In the case of an object holding method as shown in FIG. 2A, it is not possible to measure the distance corresponding to the compression distance in order to calculate the elastic modulus (Young's modulus) which was described in Example 1, and therefore the elastic modulus, and hence the average speed of sound, cannot be calculated directly. However, there is a correlation between the elastic modulus and the stress a which is determined on the basis of the pressing force (the force applied to the object) and the pressing surface area (the contact area between the holding plate and the object). Consequently, there is a correlation between the stress and the average speed of sound. As a result of this, the correlation is established in advance, in the form of a table 7a or mathematical formula. The table or formula is saved in a memory.

A processing unit 7 either determines the pressing surface area A of the object 100 from captured image data from the camera 6 or receives a pressing surface A which has been calculated in the camera. The stress σ is calculated by using the pressing surface area and the pressing force from the load cell 5, which is the force measuring unit, and the average speed of sound is determined by referring to the table 7a. The processing unit 7 then generates image data showing the object information, by using the determined average speed of sound and received signal, and an image is displayed on the monitor 8.

Figure 2B:
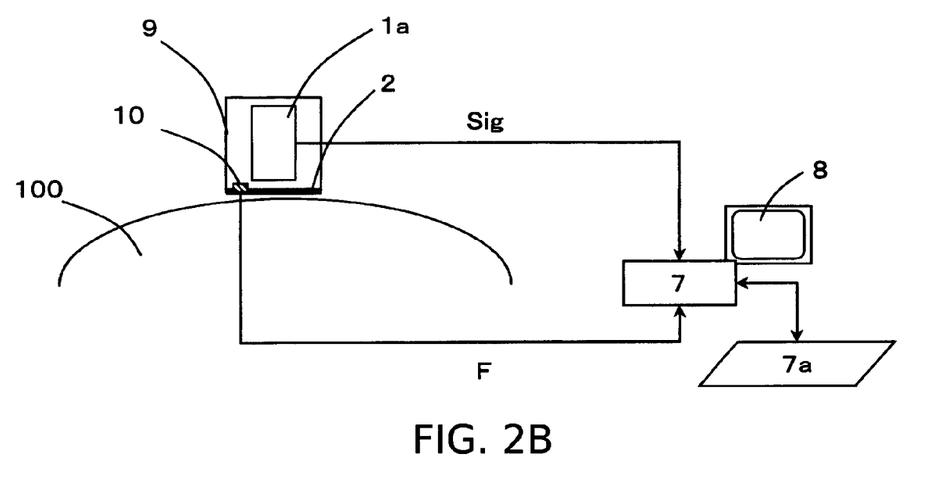
FIG. 2B is a further diagram describing the apparatus composition of Example 2.

Furthermore, this method can also be applied to a case using a handheld probe as in FIG. 2B. In FIG. 2B also, a composition is adopted in which an ultrasound wave generated from an object 100 is received by a probe element 1a, through a holding plate 2. The received signal is converted into an electrical signal which is then sent to the processing unit (Sig). The probe element 1a is accommodated inside a housing 9, and the holding plate 2 is provided in the portion of the housing 9 which contacts the object 100. A strain gauge 10 for measuring the force pressing the holding plate 2 against the object 100 is attached to the holding plate 2 or the housing 9.

In the case of FIG. 2B, the surface area A (contact area) over which the holding plate 2 presses the object 100 is the surface area of the holding plate 2, and therefore this can be treated as a known value. The processing unit 7 prepares a correlation between the pressing force and the elastic modulus or a correlation between the pressing force and the speed of sound, in the form of a table 7a. Therefore, the pressing force F (force applied to the object) is converted from an electrical signal which corresponds to the strain measured by the strain gauge 10, and the average speed of sound can be determined by referring to the table on the basis of the pressing force thus determined. Moreover, the stress σ can be derived from the determined pressing force and the known contact area, and the average speed of sound can be determined by referring to a table 7a which indicates the correlation between the stress and the speed of sound. The processing unit 7 then generates an image from the determined average speed of sound and the received signal, and displays the image on a monitor 8.

In order to apply the method shown in FIG. 2A and FIG. 2B to PAM, illumination light should be irradiated from the probe 1.

In this way, according to Example 2, it is possible to install a mechanism for determining the average speed of sound in an object, even in living organism information acquiring apparatuses of various kinds other than one based on a parallel flat plate compression and holding system.

Example 3

Figure 3:
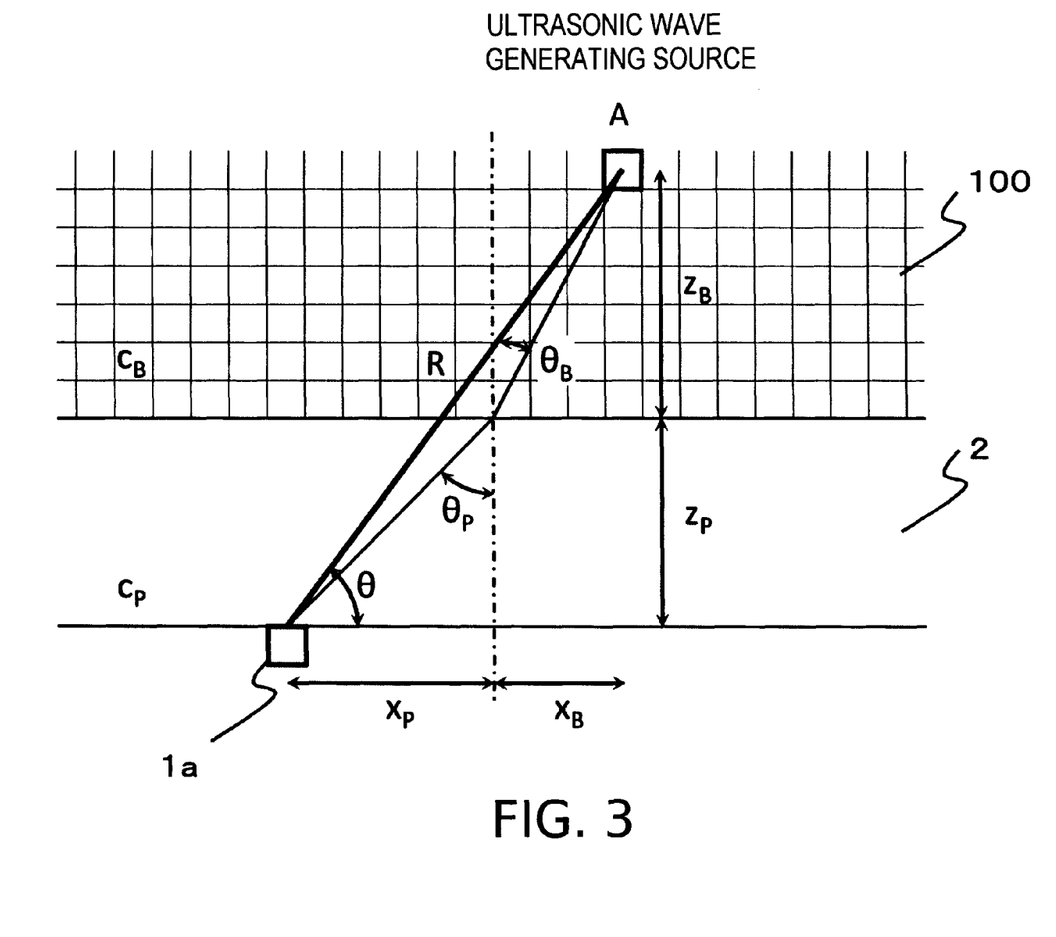
FIG. 3 is a diagram describing refraction of an acoustic wave in Example 3.

Example 3 describes, with reference to FIG. 3, a case where the speed of sound in a holding plate 2 (the speed of sound inside a holding unit) differs from the speed of sound inside an object 100. If the speed of sound is different in the holding plate 2 and the object 100, then the ultrasound wave is diffracted. If refraction of the ultrasound wave occurs, then there is variation in the distance and angle from the ultrasound wave generating source to the probe element. Therefore, resolution will decline unless the image is corrected to account for the refraction. In this correction, in order to select suitable data from the target of which an image is generated, it is necessary to specify the relationship between the (apparent) position of the ultrasound wave generating source which is determined, and the actual position of the ultrasound wave generating source. Furthermore, it is necessary to specify the relationship between the correct position of the ultrasound wave generating source based on the angle of refraction and the travel time of the ultrasound wave.

The holding plate 2 is desirably made of polymethylpentene (PMP), and the speed of sound therein is approximately 2200 m/s. In an object 100 to which a compression force (pressing force) is not applied (in the case of a breast), the speed of sound is approximately 1510 m/s, and therefore the ultrasound wave is diffracted, as shown in FIG. 3. This refraction should be corrected on the basis of Snell's law, as indicated below.

In the Formula given below, τ is the travel time of the ultrasound wave from the ultrasound wave generating source to the probe element 1a, and R is the travel distance in this case. c is the average speed of sound, z is the depth (thickness), x is the distance in the surface direction, and θ is the angle of refraction. Furthermore, the suffix letters B and P respectively indicate the object 100 and the holding plate 2. For example, $c_B$ is the average speed of sound in the object and $c_P$ is the average speed of sound in the holding plate. The speed of sound $c_P$ in the holding plate 2 and the thickness $z_P$ of the holding plate 2 are known as uniform values, depending on the material.

The travel time τ of the ultrasound wave from the ultrasound wave generating source to the probe element 1a is expressed in relation to the angle of refraction and the depth. τ is the sum of the travel time of the ultrasound wave from the ultrasound wave generating source to the refraction surface, and the travel time of the ultrasound wave from the refraction surface to the probe element, and is therefore expressed as shown in Formula (5).

[Math. 2]

$$\tau = \frac{z_B}{c_B}\frac{1}{\cos\theta_B} + \frac{z_P}{c_P}\frac{1}{\cos\theta_P} \quad (5)$$

Here, from Snell's law, Formula (6) is established.

[Math. 3]

$$\frac{c_B}{c_P} = \frac{\sin\theta_B}{\sin\theta_P} \quad (6)$$

Furthermore, the angle of refraction is expressed by Formula (7) and Formula (8) below.

[Math. 4]

$$\theta_P = \tan^{-1}\frac{x_P}{z_P} \quad (7)$$

$$\theta_B = \tan^{-1}\frac{x_B}{z_B} \quad (8)$$

Consequently, the positional relationship between the probe element and the actual position of the ultrasound wave generating source is expressed as shown in Formula (9).

[Math. 5]

$$x_P + x_B = R\cos\theta \quad (9)$$

If the relationship described above is used, then it is possible to correct the data by determining the actual position in the object and the actual time at which the ultrasound wave reaching the probe element was produced. Consequently, when generating an image, it is possible to select accurate data corresponding to the target.

The average speed of sound $c_B$ in the object 100 changes when a compression force (pressing force) is applied to the object 100, as described in Example 1 and Example 2. Therefore, rather than calculating the speed of sound in the object 100 as 1510 m/s, it is possible to determine the average speed of sound by the method described in Example 1 or Example 2, and to apply this value of the speed of sound as the value of $c_B$ in the Formulas given above. In so doing, it is possible to correct refraction more accurately, which is desirable from the viewpoint of improving the resolution.

In this way, according to Example 3, it is possible to correct refraction of the ultrasound wave produced as a result of the difference in the speed of sound in the holding plate 2 and the object 100, and therefore the resolution of the imaging process is improved.

As a further method for achieving this, if the compression force (pressing force) on the object 100 is raised until the average speed of sound in the object 100 becomes substantially equal to the speed of sound of the holding plate 2 ($c_B \cong c_P$), then when generating an image, it is possible to calculate the speed of sound as the value of 2200 m/s in polymethyl pentene. Therefore, without lowering the resolution, it is unnecessary to correct refraction of the ultrasound waves, and therefore the calculation processing time can be shortened.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-204380, filed on Sep. 13, 2010, and Japanese Patent Application No. 2011-171913, filed on Aug. 5, 2011, which are hereby incorporated by reference herein in their entirety.

The invention claimed is:

1. An object information acquiring apparatus, comprising:
a holding unit configured to hold an object, wherein said holding unit includes two plates and being configured to compress and hold the object by said two plates;
a probe configured to receive an acoustic wave generated in the object via said holding unit and convert the acoustic wave to an electrical signal;
a force measuring unit configured to measure a force applied to the object when the object is held by said holding unit;
an area measuring unit configured to measure a contact area between the object and said holding unit;
a distance measuring unit configured to measure a distance between said two plates; and
a sound speed acquiring unit configured to acquire a sound speed in the object by using the force measured by said force measuring unit, the contact area between the object and said holding unit measured by said area measuring unit, and the distance between said two plates as measured by said distance measuring unit before and after said two plates compress the object.

2. The object information acquiring apparatus according to claim 1, wherein said sound speed acquiring unit is configured to acquire a stress on the object by using the force measured by said force measuring unit and the contact area measured by said area measuring unit, and to acquire the sound speed in the object by using the stress on the object.

3. The object information acquiring apparatus according to claim 1, wherein said holding unit is a member which is pressed against the object.

4. The object information acquiring apparatus according to claim 1, further comprising a housing which accommodates said probe, wherein one of said two plates is provided at a position where said housing makes contact with the object.

5. The object information acquiring apparatus according to claim 1, further comprising a memory which holds a table or formula expressing a relationship between the sound speed in the object, the force applied to the object, the contact area between the object and said holding unit and the distance between said two plates,
wherein said sound speed acquiring unit is configured to acquire the sound speed in the object by using said table or formula held in said memory, the force measured by said force measuring unit, the contact area measured by said area measuring unit, and the distance measured by said distance measuring unit.

6. The object information acquiring apparatus according to claim 1, wherein the acoustic wave is an acoustic wave generated in the object which is illuminated with light.

7. The object information acquiring apparatus according to claim 1, wherein the acoustic wave is an ultrasound wave which has been transmitted to the object and reflected.

8. The object information acquiring apparatus according to claim 1, further comprising a generating unit configured to generate object information data by using the sound speed in the object acquired by said sound speed acquiring unit and the electrical signal.

9. The object information acquiring apparatus according to claim 8, wherein said generating unit is configured to generate the object information data by performing a correction process of refraction based on the sound speed in the object.

10. An object information acquiring apparatus, comprising:
a holding unit configured to hold an object;
a probe configured to convert an acoustic wave generated in the object and received via said holding unit and into an electrical signal;
a memory which holds a table or formula expressing a relationship between a stress on the object and a sound speed in the object;
a force measuring unit configured to measure a force applied to the object when the object is held by said holding unit;
an area measuring unit configured to determine a contact area between the object and said holding unit by use of light or acoustic wave; and
a sound speed acquiring unit configured to acquire the stress on the object by using the force measured by said force measuring unit and the contact area measured by said area measuring unit, and to acquire the sound speed in the object by using the stress on the object and said table or said formula held in said memory.

11. The object information acquiring apparatus according to claim 10, wherein said holding unit has a cup shape.

12. The object information acquiring apparatus according to claim 10, further comprising a housing which accommodates said probe, wherein said holding unit is a plate provided at a position where said housing makes contact with the object.

13. The object information acquiring apparatus according to claim 10, wherein the acoustic wave is an acoustic wave generated in the object which is illuminated with light.

14. An object information acquiring apparatus, comprising:
a holding unit configured to hold an object;
a probe configured to convert an acoustic wave generated in the object and received via said holding unit into an electrical signal;
a memory which holds a table or formula expressing a relationship between a force applied to the object, a contact area between the object and said holding unit, and a sound speed in the object;
a force measuring unit configured to measure the force applied to the object when the object is held by said holding unit;
an area measuring unit configured to measure the contact area between the object and said holding unit by using light or acoustic wave; and
a sound speed acquiring unit configured to acquire the sound speed in the object by using the force measured by said force measuring unit, the contact area measured by said area measuring unit, and said table or said formula held in said memory.

15. The object information acquiring apparatus according to claim 14, wherein said holding unit has a cup shape.

16. The object information acquiring apparatus according to claim 14, further comprising a housing which accommodates said probe, wherein said holding unit is a plate provided at a position where said housing makes contact with the object.

17. The object information acquiring apparatus according to claim 14, wherein the acoustic wave is an acoustic wave generated in the object which is illuminated with light.

18. An object information acquiring apparatus, comprising:
a holding unit configured to hold an object;
a probe configured to convert an acoustic wave generated in the object and received via said holding unit into an electrical signal;
a memory which holds a table or formula expressing a relationship between a force applied to the object and a sound speed in the object;
a force measuring unit configured to measure the force applied to the object when the object is held by said holding unit; and
a sound speed acquiring unit configured to acquire the sound speed in the object by using the force measured by said force measuring unit and said table or said formula held in said memory.

19. The object information acquiring apparatus according to claim 18, wherein said holding unit has a cup shape.

20. The object information acquiring apparatus according to claim 18, further comprising a housing which accommodates said probe, wherein said holding unit is a plate provided at a position where said housing makes contact with the object.

21. The object information acquiring apparatus according to claim 18, wherein the acoustic wave is an acoustic wave generated in the object which is illuminated with light.

* * * * *